United States Patent [19]
Bogert

[11] Patent Number: 5,599,310
[45] Date of Patent: Feb. 4, 1997

[54] I.V. CATHETER ASSEMBLY WITH AUTOMATIC CANNULA TIP GUARD

[75] Inventor: David L. Bogert, Plainville, Conn.

[73] Assignee: Johnson & Johnson Medical, Inc., Arlington, Tex.

[21] Appl. No.: 482,590

[22] Filed: Jun. 7, 1995

[51] Int. Cl.$^6$ .................................................. A61M 5/00
[52] U.S. Cl. .......................... 604/164; 604/198; 604/263
[58] Field of Search .......................... 604/164, 165–171, 604/192, 187, 198, 263, 53, 264, 110

[56] References Cited

U.S. PATENT DOCUMENTS

| | | |
|---|---|---|
| 4,117,809 | 1/1982 | Moorehead . |
| 4,762,516 | 8/1988 | Luther et al. . |
| 4,790,828 | 12/1988 | Dombrowski et al. . |
| 4,804,371 | 2/1989 | Vaillancourt . |
| 4,826,490 | 5/1989 | Byrne et al. . |
| 4,832,696 | 5/1989 | Luther et al. . |
| 4,834,718 | 5/1989 | McDonald . |
| 4,917,669 | 4/1990 | Bonaldo . |
| 4,931,048 | 6/1990 | Lopez . |
| 4,944,725 | 7/1990 | McDonald . |
| 4,950,252 | 8/1990 | Luther et al. . |
| 4,952,207 | 8/1990 | Lemieux . |
| 4,964,854 | 10/1990 | Luther . |
| 4,978,344 | 12/1990 | Dombrowski et al. . |
| 4,994,041 | 2/1991 | Dombrowski et al. . |
| 5,007,901 | 4/1991 | Shields . |
| 5,084,023 | 1/1992 | Lemieux . |
| 5,084,030 | 1/1992 | Byrne et al. . |
| 5,127,905 | 7/1992 | Lemieux . |
| 5,205,829 | 4/1993 | Lituchy . |
| 5,215,528 | 6/1993 | Purdy et al. . |
| 5,250,035 | 10/1993 | Smith et al. ........................ 604/164 |
| 5,308,336 | 5/1994 | Hart et al. ........................ 604/167 |
| 5,312,371 | 5/1994 | Dombrowski et al. . |
| 5,312,376 | 5/1994 | Van Heugten . |

*Primary Examiner*—John D. Yasko
*Attorney, Agent, or Firm*—Joseph F. Shirtz

[57] ABSTRACT

A catheter assembly comprising a catheter attached to a catheter hub, a cannula insertable into the catheter through the catheter hub and a tip guard providing automatic protection of the cannula tip and automatic locking and releasing of the tip guard form the catheter hub. The tip guard includes a base and a plurality of resilient fingers extending from the base which are adapted to flex radially outwardly to allow the cannula to be inserted in the hub and which return to the spring biased position when the cannula is withdrawn from the catheter into the guard to secure the catheter within the guard. A detent on the distal ends of the fingers engages corresponding recesses in the catheter hub to lock the tip guard in the hub when the cannula is inserted through the guard.

12 Claims, 7 Drawing Sheets

I.V. CATHETER ASSEMBLY WITH AUTOMATIC CANNULA TIP GUARD

BACKGROUND OF THE INVENTION

This invention relates to intravenous (I.V.) catheter assemblies and, in particular, to a catheter assembly having a cannula tip guard which automatically covers the cannula tip after use to prevent accidental injury from used cannulas.

Intravenous catheters for the infusion of fluids into the peripheral veins of a patient are one the most common devices used in I.V. therapy. In one type of catheter known as an over-the-needle catheter, the cannula and concentric outer catheter are inserted into the vein and the cannula is withdrawn through the emplaced catheter.

A typical over-the-needle I.V. catheter requires the user to remove and then dispose of a contaminated cannula after the cannula tip and catheter are properly located in the vein of the patient. Once the cannula is withdrawn from the catheter, the user's immediate priorities are infusion set connection and site preparation, including the taping of the catheter to the patient. Because of the urgency of these procedures the cannula is normally just dropped conveniently nearby and then retrieved later. Since the cannula at this time is exposed and located close to where the user is completing work with the catheter, accidental self-inflicted injuries are not uncommon. For reasons of the desirability of protecting the user from exposure to hepatitis and AIDS, there is an increasing need to protect the user from accidental cannula injury.

A catheter design which is directed toward this need is shown in U.S. Pat. No. 4,762,516. The catheter shown in this patent includes an elongate body which houses a sliding needle guard. As the needle is withdrawn from the emplaced catheter, the user pushes the tab at the distal end of the needle guard, thereby sliding the needle guard out of the housing and along the needle, until the distal end of the guard covers the needle tip and the proximal end of the guard locks in the housing. The needle and guard may then be set aside with the needle tip fully protected.

Another needle guard is shown in U.S. Pat. No. 5,084,023. The needle guard in this patent includes a sleeve having a locking ring to secure the guard to a return valve assembly. The guard also includes a notch that engages a corresponding recess is the needle to prevent the needle from being withdrawn from the guard.

U.S. Pat. No. 4,834,718 also discloses a needle tip guard. A hub portion of the guard of this patent mounts within the catheter hub and includes a resilient tongue. The tongue flexes outward to engage a recess in the catheter hub when the needle is inserted through the guard. When the needle is withdrawn into the guard, the tongue flexes inward releasing the guard from the hub. The guard is further comprised of a housing that extends the entire length of the blood chamber. A latching mechanism on the extreme end of the housing holds the needle tip within the guard.

While the arrangements described in the above prior art patents provide protection against accidental needle injury, the requirements of each of these devices necessarily requires rather long and/or bulky assemblies. Moreover, the arrangements are somewhat cumbersome to operate for users with small hands and fingers.

Accordingly, it would be desirable for a needle to be securely protected by a small needle guard, and it would be most preferable for the needle guard to be moved into position over the needle tip automatically upon withdrawal of the needle from the patient, without the intervention of any special motion by the user.

SUMMARY OFT HE INVENTION

The present invention is directed to an I.V. catheter with an automatic cannula guard that utilizes a collapsing nose design. In accordance with the present invention there is provided a catheter assembly comprising a catheter attached to the catheter hub. A cannula having a distal tip is insertable into the catheter through the catheter hub. A tip guard having a base and a plurality of resilient fingers extending from the base provides automatic protection against accidental needle sticks after withdrawal of the cannula from the catheter. The plurality of fingers are spring biased so that a distal end of each of the fingers is in contact thereby forming a closed chamber within the tip guard. The fingers are adapted to flex radially outwardly to permit the cannula to be inserted into the catheter hub through the tip guard. The fingers return to the spring biased contact position when the distal tip of the cannula is withdrawn from the catheter into the tip guard thereby securing the distal tip within the closed chamber. In addition, locking means is provided for engaging the tip guard to the catheter hub when the cannula is inserted through the catheter hub. The locking means is adapted to release the tip guard from the catheter hub when the distal tip of the cannula is withdrawn from the catheter into the tip guard.

In an alternative embodiment, the plurality of fingers of the tip guard are spring biased to form a passageway from the base of the guard to the distal end of each of the fingers. The passageway has a diameter smaller than the diameter of the catheter. An addition, each of the fingers has a channel extending from the base to a location spaced from the distal end of the fingers. The finger channels form a chamber having a diameter substantially equal to the diameter of the cannula. The fingers are adapted to flex radially outwardly to permit the cannula to be inserted into the catheter through the tip guard. The fingers return to the spring biased position when the distal tip of the cannula is withdrawn from the catheter into the tip guard thereby securing the distal tip within the chamber to prevent the distal tip of the cannula from being reinserted through the distal ends of the of the tip guard fingers.

The locking means is provided by a detent on the distal ends of the fingers and a corresponding recess in the catheter hub. When the fingers flex radially outwardly to permit the cannula to be inserted into the catheter hub, the detent on the fingers engages the hub in the recess. The thickness of the cannula causes the fingers to remain in that flexed position thereby locking the tip guard into the hub.

The catheter assembly further includes a cannula housing engaging the cannula on a proximal end of the cannula, a blood flash chamber attached to the cannula housing and a cannula guard. The cannula guard is attached to the tip guard and extends radially over only a portion of the cannula. Preferably, the cannula guard extends over less than half the circumference of the cannula permitting a low, oblique angle of insertion.

DETAILED DESCRIPTION OF THE INVENTION

Figure 1:
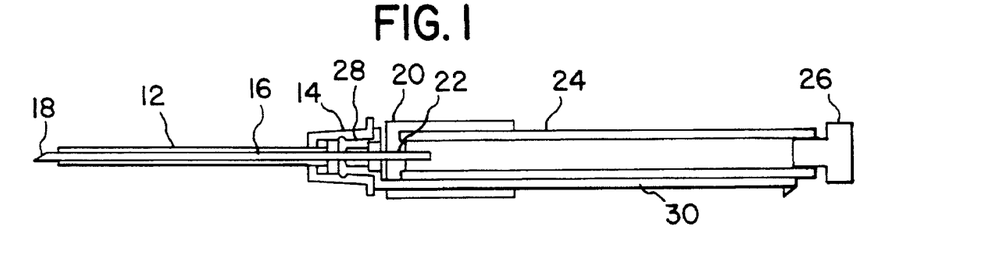
FIG. 1 is a schematic cross sectional view of the catheter assembly of the present invention.

Referring now to the drawings, FIG. 1 is a schematic side view of the catheter assembly 10 of the present invention. Catheter assembly 10 includes a catheter 12 attached to a catheter hub 14. A cannula 16 having a distal sharp tip 18 is insertable into the catheter 12 through the catheter hub 14. the catheter assembly 10 also includes a catheter housing 20 that engages a proximal end 22 of the cannula for insertion and withdrawal of the cannula into and out of the catheter 12. A blood flash chamber 24 is attached to the housing 20 and is sealed on its open end with plug 26. The catheter assembly 10 further includes a tip guard 28 and a cannula guard 30.

Figure 2A:
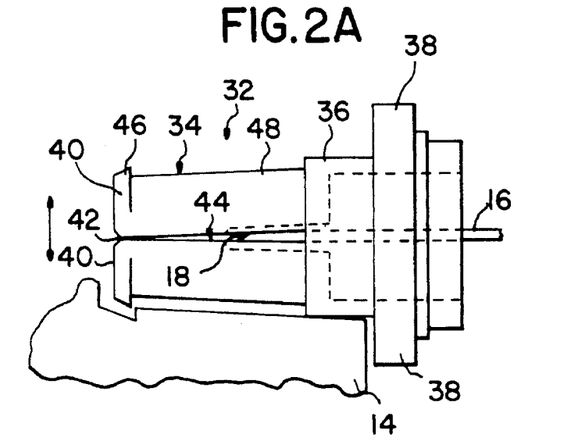
FIGS. 2(a) and 2(b) are a side elevational and an end view of one embodiment of the tip guard of the present invention.
Figure 2B:
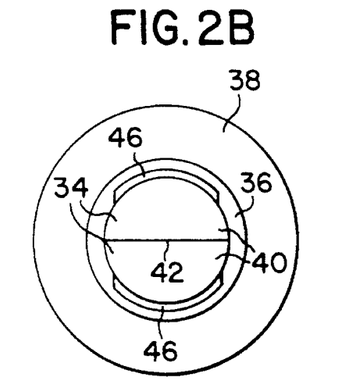
Figure 3:
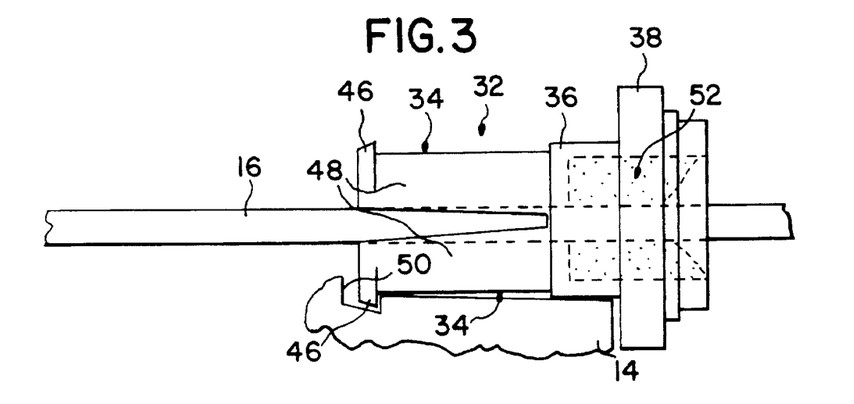
FIG. 3 is a side elevational view of the tip guard shown in FIGS. 2A and 2B with the cannula inserted through the tip guard.

FIGS. 2(a), 2(b), and 3 show detailed views of one embodiment of the tip guard of the present invention. Tip guard 32 includes a plurality of resilient fingers 34 that extend from a base 36. The tip guard 32 also includes mounting flange 38 that rests against the catheter hub 14 and a portion 39 that attaches into the housing 22. Although two fingers 34 are shown in FIG. 2(a), it is understood that three or more fingers may be provided. The plurality of fingers 34 are spring biased so that the distal ends 40 of each of the fingers is in contact as shown at 42, thereby forming a closed chamber 44 within the tip guard 32. The fingers 34 are adapted to flex radially outwardly as shown in FIG. 3 to permit the cannula 16 to be inserted into the catheter hub 14 through the tip guard 32. The fingers 34 are flexed radially outwardly by mechanical means such as angled jaws, wide enough to allow the cannula to pass through the tip guard with out touching the guard.

Each of the fingers 34 includes a detent 46 extending radially outwardly from each of the finger bodies 48. The detents 46 fit within corresponding recesses 50 in the catheter hub 14 when the cannula 16 is inserted through the tip guard 32 as shown in FIG. 3. The combination of the detents 46 mating within recesses 50 and the flange 38 abutting hub 14 locks the tip guard 32 within the catheter hub 14. As shown in FIG. 2(a), when the cannula 16 is-withdrawn from the catheter such that the tip 18 is positioned within the chamber 44, the spring biasing of the fingers 34 causes the distal ends 40 to again contact each other at 42 with the cannula tip 18 secured within the closed chamber 44. Thus, the tip guard 32 provides both an automatic tip protection mechanism when the cannula is withdrawn from the catheter as well as an automatic locking mechanism for engaging the tip guard to the catheter hub when the cannula is inserted in the catheter. A gasket 52 is provided within the base of the tip guard for sealing the cannula within the tip guard.

Figure 4:
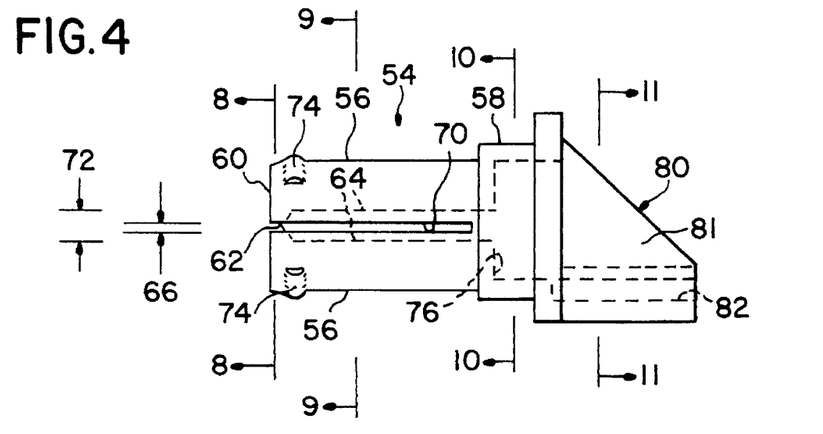
FIG. 4 is a side elevational view of a second embodiment of the tip guard of the present invention.

FIGS. 4–11 show an alternative embodiment of the tip guard of the present invention. As shown in FIG. 4, tip guard 54 includes a plurality of fingers 56 extending from base 58 to their distal ends 60. The fingers 56 are spring biased to form a passageway 62 extending from base 58 to the distal ends 60 of each of the fingers. Each of the fingers 56 also includes a channel 64. The diameter 66 of the passage way 62 is smaller than the diameter 68 of the cannula 16. The combination of the channels 64 form a chamber 70 that has a diameter 72 substantially equal to the diameter 68 of the cannula 16. The fingers 56 also include detents 74 for locking into corresponding recesses in the catheter hub (not shown).

Figure 5:
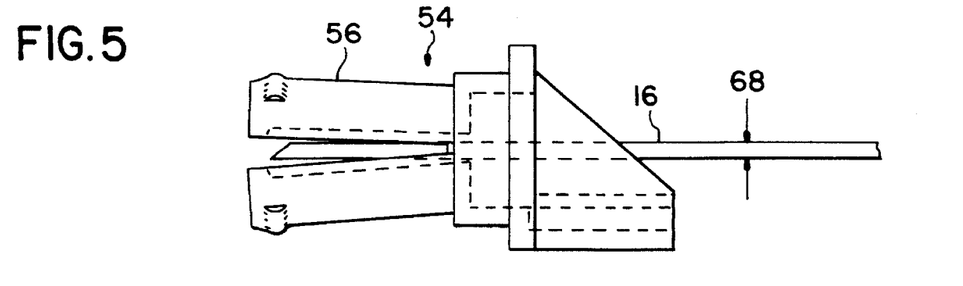
FIGS. 5, 6 and 7 are side elevational views of the tip guard of FIG. 4 showing the insertion and withdrawal of a cannula.
Figure 6:
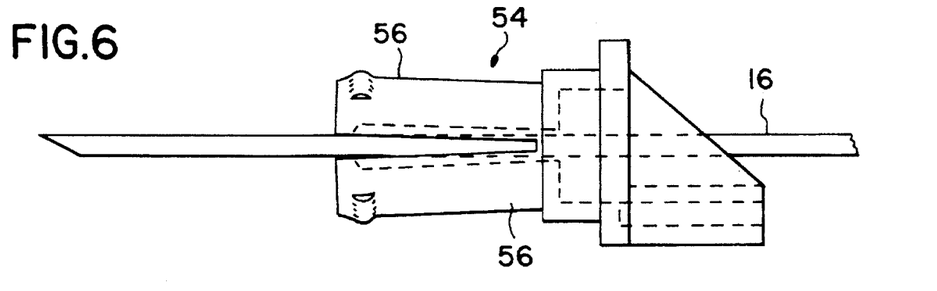
Figure 7:
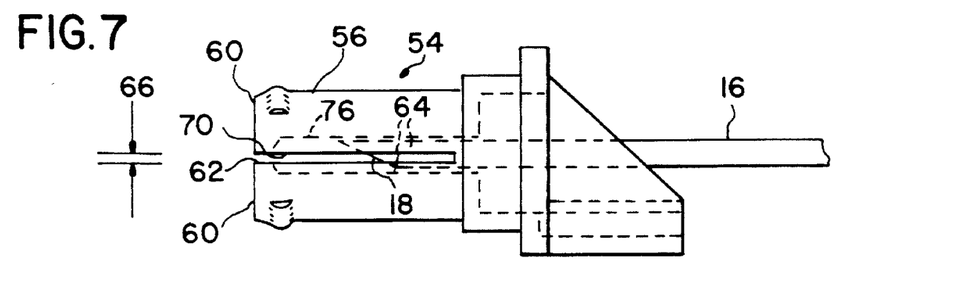

As shown in FIG. 5, the fingers 56 are adapted to flex radially outwardly to permit the cannula 16 to be inserted through the tip guard 54. As stated above, mechanical means such as angled jaws are used to flex the fingers radially outwardly sufficient to permit the cannula to pass through the tip guard without touching the fingers 56. As shown in FIG. 6, after the cannula 16 is inserted through the tip guard 54 the fingers 56 are released from the angled jaws and spring back to contact the outer surface of the cannula 16. The fingers 56 in this position are slightly radially expanded thereby putting a slight spring tension on the cannula. This tension provides a snug fit but still permits the cannula to be inserted further into the catheter and withdrawn from the catheter through the tip guard 54. As shown in FIG. 7, once the cannula 16 is withdrawn such that the tip is within the tip guard 54 the fingers 56 spring back to their original biased position. The cannula 16 then becomes secured within the chamber 70 formed by the channels 64. As can be seen in FIG. 7, the passageway 62 is smaller in diameter than the outside diameter of the cannula 16 and is prevented from being reinserted through the distal ends 60 of the fingers 56. If reinsertion is attempted, the tip 18 will abut against the end walls 76 of the channels 64 and therefore cannot re-emerge from the tip guard 54.

Figure 8:
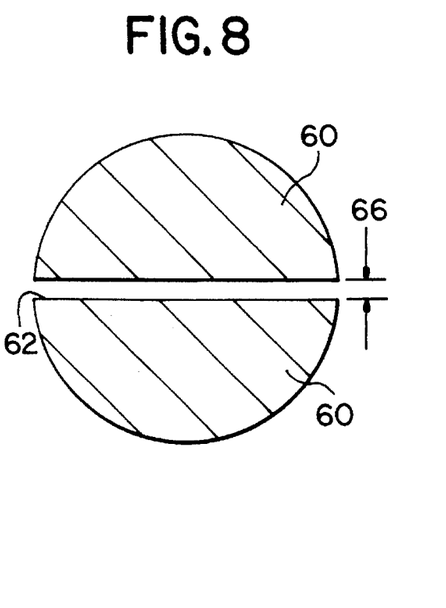
FIGS. 8, 9, 10 and 11 are cross sectional views taken along the corresponding lines of the tip guard shown in FIG. 4.
Figure 9:
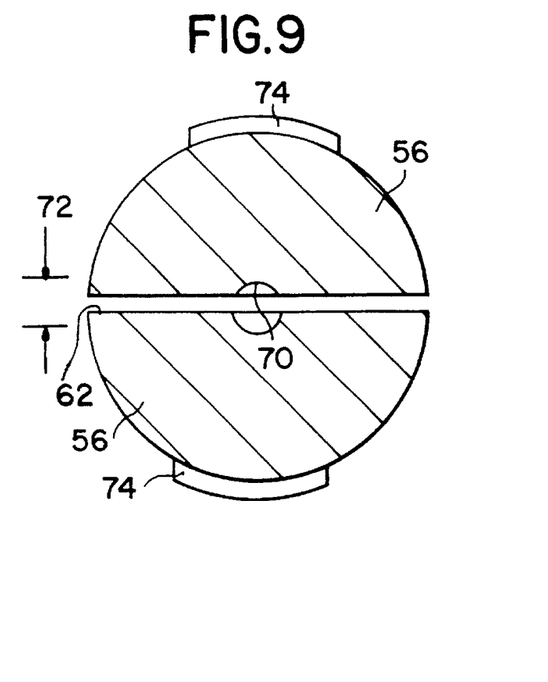
Figure 10:
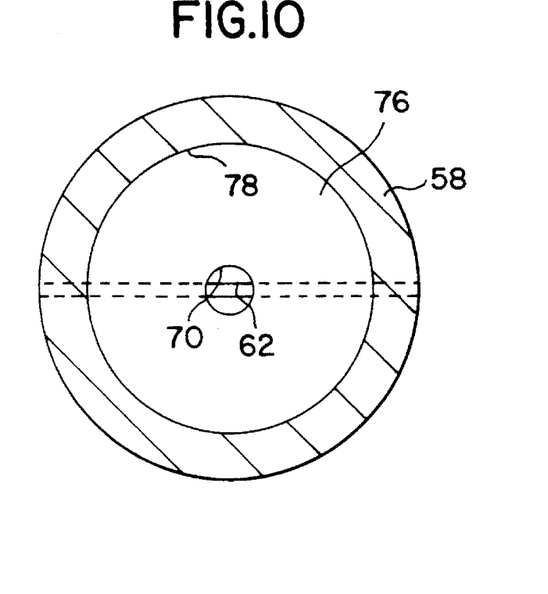
Figure 11:
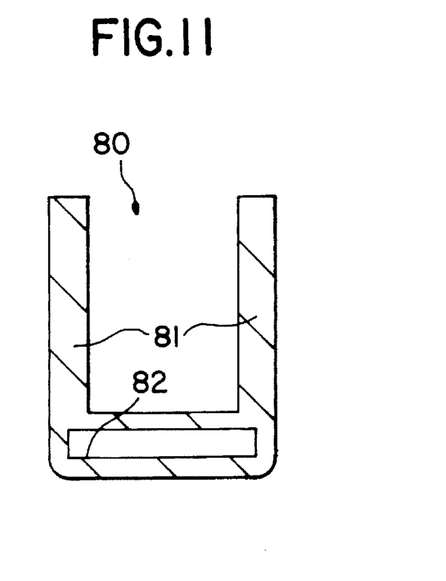

FIG. 8 is a cross sectional view of the tip guard 54 of FIG. 4 taken along Lines 8—8. The distal ends 60 are shown with the passageway 62 having a diameter 66. FIG. 9 shows a cross sectional view of the tip guard 54 of FIG. 4 taken along Lines 9—9. Fingers 56 are shown with detents 74 protruding from the finger bodies for engaging the corresponding recesses in the catheter hub. Chamber 70 is shown which has a diameter 72 smaller than the diameter 66 of passageway 62. FIG. 10 is a cross sectional view taken along Lines 10—10 of FIG. 4 which shows the base 58 and includes a gasket 76 contained in a gasket well 78. The passageway 62 and channel 70 are visible through a central opening in the gasket 76. FIG. 11 is a cross sectional view of a rear portion 80 of the tip guard 54 taken along lines 11—11 of FIG. 4. A slot 82 is provided for attaching cannula guard 30 to the tip guard 54 by means of a press fit. The rear portion 80 in this embodiment is comprised of a U-shaped member having triangular ribs 81, which fit into complementary slots in housing 22.

Figure 12:
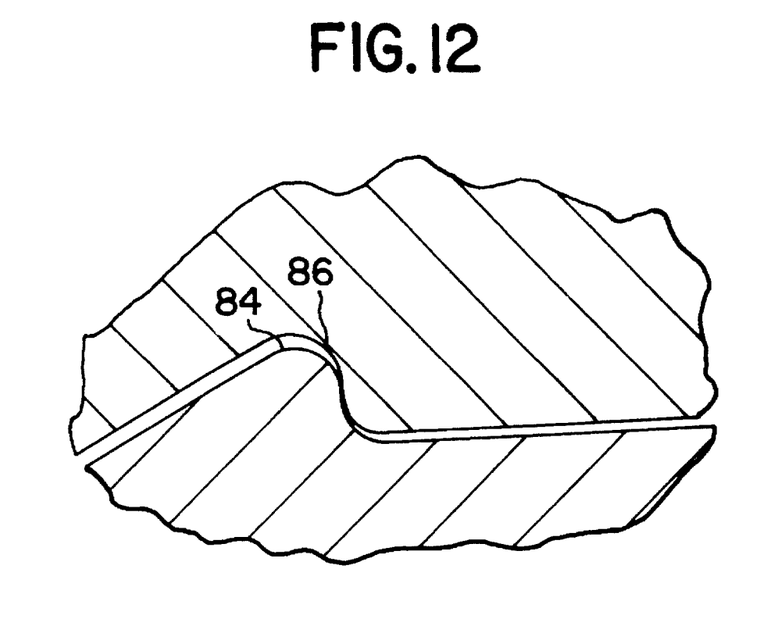
FIG. 12 is a cross sectional view of one embodiment of the means for locking the tip guard into the catheter hub.

As noted above, the detent on the fingers and the corresponding recess in the catheter hub provide the locking means to engage the tip guard to the catheter hub. The detent recess construction shown for example in FIG. 3 has a relatively severe depth and angle. An alternative construction is shown in FIG. 12 wherein a very shallow, rounded detent 84 and corresponding recess 86 are provided. For example, the detent and recess can be as small as 0.002 to 0.008 in depth. A shallow detent recess would simplify molding so that a straight pull and a simple mold for both the tip guard and the catheter hub can be used. In addition, a rounded design will allow the tip guard to be removed from the catheter hub prematurely with some force, if necessary, but would not easily be disengaged. In the mold for forming a founded detent tip guard the undercut can be easily stripped by pulling the blades forming the core. Pulling these blades would leave a gap in the plastic that would allow easy ejection of the undercut.

Figure 13:
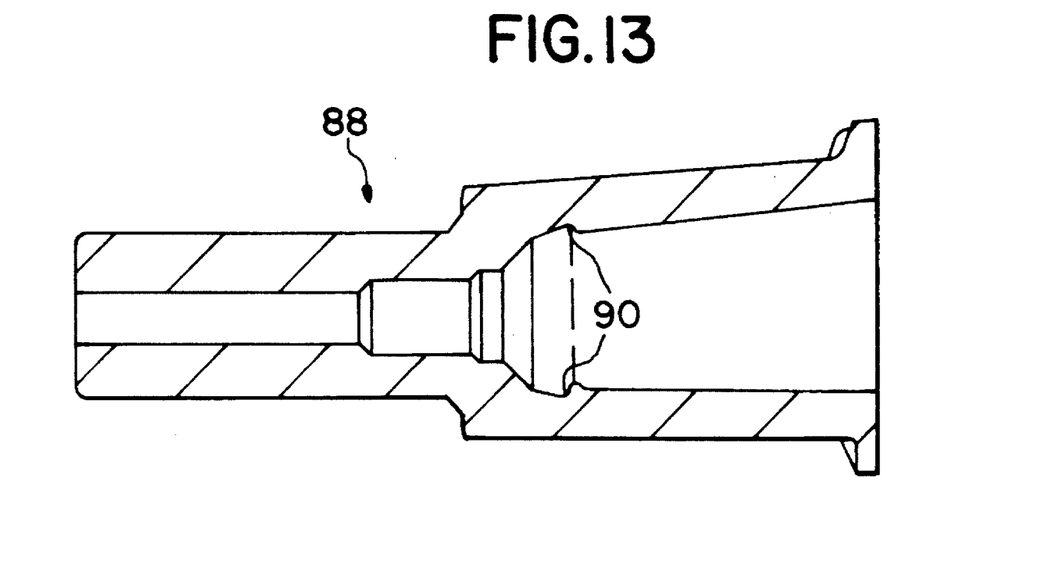
FIG. 13 is a cross sectional view of the catheter hub of the catheter assembly of the present invention.

FIG. 13 shows a basic Catheter hub 88 with the only difference between the standard hub and the hub utilized in the present invention is the recess 90. As with the tip guard, if a rounded recess is provided a straight pull in the mold could be used with no collapsing coils or special tooling.

Figure 14:
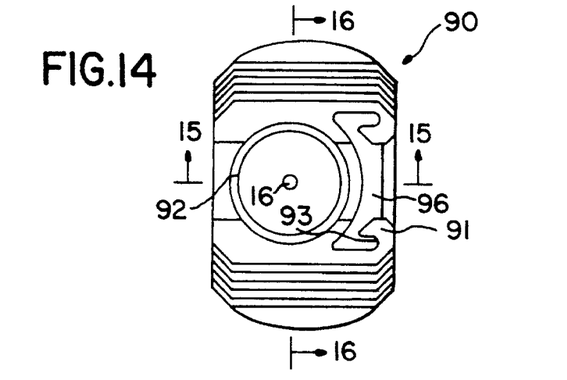
FIG. 14 is and end view of the catheter housing of the catheter assembly of the present invention.
Figure 15:
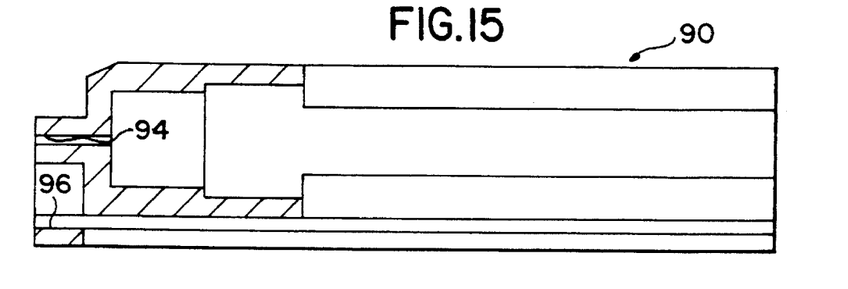
FIGS. 15 and 16 are cross sectional views of the housing taken along the corresponding lines of FIG. 14.
Figure 16:
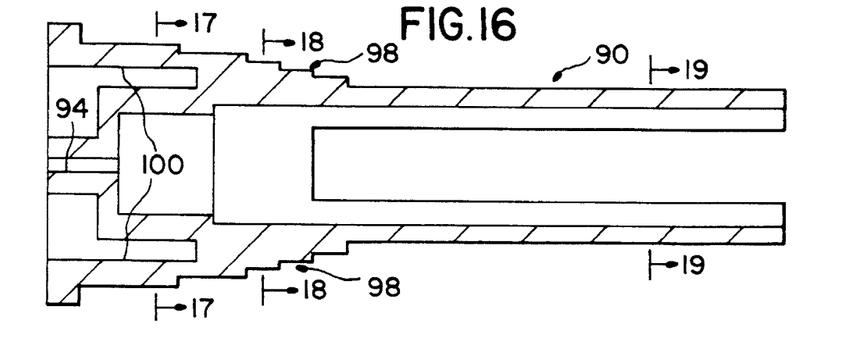
Figure 17:
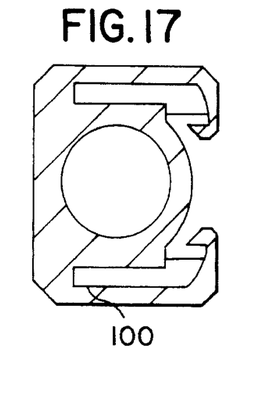
FIGS. 17, 18 and 19 are cross sectional views of the housing taken along the corresponding lines shown in FIG. 16.
Figure 18:
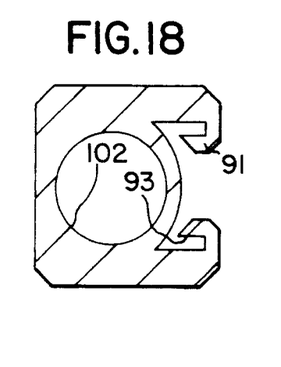
Figure 19:
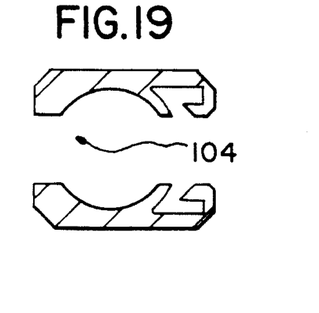

FIGS. 14–19 show one embodiment of the catheter housing 20 shown in FIG. 1. An end view of the housing 90 is shown in FIG. 14. The cannula 16 runs through the center of the housing and the recess 92 is provided for receiving the blood flash chamber. Detents 91 and grooves 93 hold the cannula guard in place and together with slot 96 allow it to move forward and backward smoothly. FIG. 15 is a cross sectional view of the housing 90 taken along Lines 15—15 of FIG. 14. The passageway 94 is provided for inserting the cannula, and slot 96, as stated above, receives the cannula guard. FIG. 16 is a cross sectional view of the housing 90 taken along Lines 16—16 of FIG. 14. Stepped regions 98 provide finger holes where the user grips the housing in order to insert the cannula into the catheter and to remove the cannula from the catheter. Slots 100 receive ribs 81 on the tip guard. FIG. 17 is a cross sectional view taken along Lines 17—17 of FIG. 16 which shows slots 100 for receiving triangular ribs 81 holding the tip guard secure to the cannula guard. A hole 102 is provided to accept the blood chamber. FIG. 18 is a cross sectional view taken along Lines 18—18 of FIG. 16 which shows the hole 102, the detents 91 and the grooves 93. FIG. 19 is a cross sectional view taken along Lines 19—19 of FIG. 16 which shows area 104 cut out to allow easy molding with no steel deflections.

Figures 20A, 20B:
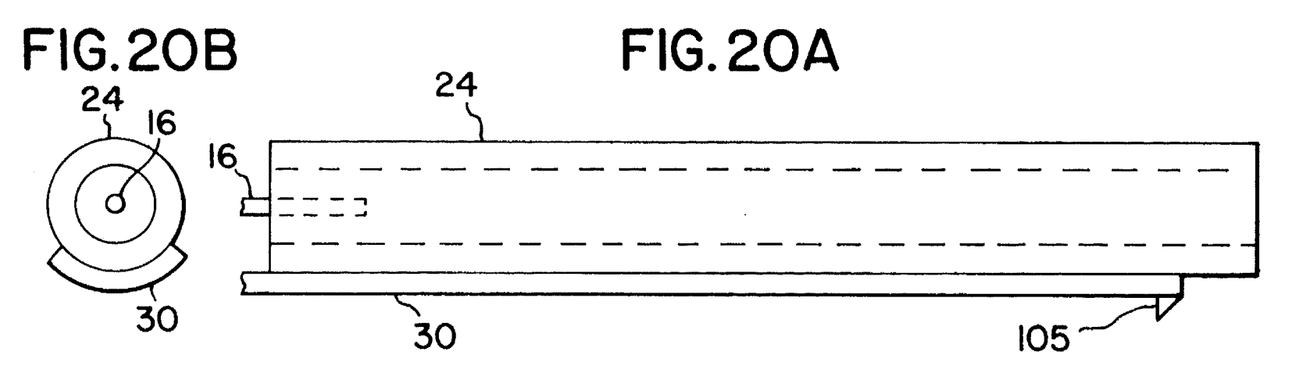
FIGS. 20(a) and 20(b) are a side elevational view and an end view of the blood flash chamber and cannula guard of the catheter assembly of the present invention.

While the tip guard will completely surround and encapsulate the sharp point or tip of the cannula, the cannula guard in accordance with another aspect of the present invention will only surround the shaft of the cannula on one side. This feature of the invention is shown in FIGS. 20(a) and 20(b). FIG. 20(a) shows the cannula 16 partially extending within the blood flash chamber 24. The cannula guard 30 does not completely surround the cannula 16 or blood flash chamber 24 but only surrounds a portion of the cannula 16. In the preferred embodiment the cannula guard 30 surrounds less than half of the circumference of the cannula 16. Having the cannula guard only on one side of the cannula allows for a light, slim and trim catheter assembly that permits a low angle of insertion. Also shown in FIG. 20(a) is the detent 105 that limits the forward movement of the guard with respect to the housing.

The catheter assembly of the present invention provides many advantages over the prior art. The collapsing nose design provides an automatic protection mechanism that protects the tip of the cannula irregardless of the insertion technique. In addition, the tip guard also provides an automatic locking of the guard to the catheter hub. The catheter assembly is slim, light and trim and allows for a very low, oblique angle of insertion. The assembly has a very large, long, flushable, easily seen blood flash chamber. Moreover, the palm of the hand is prevented from moving the catheter on the cannula during insertion. The user can see the cannula directly during insertion as there is clear material and/or a color difference between the cannula mechanism and the guard mechanism so that operation is intuitive. The catheter assembly of the present invention is inexpensive and simple to tool and mold as well as assemble. The one sided guard permits the blood chamber to be very large. In addition the blood chamber is longer than the cannula guard preventing accidental advancement.

Figure 21:
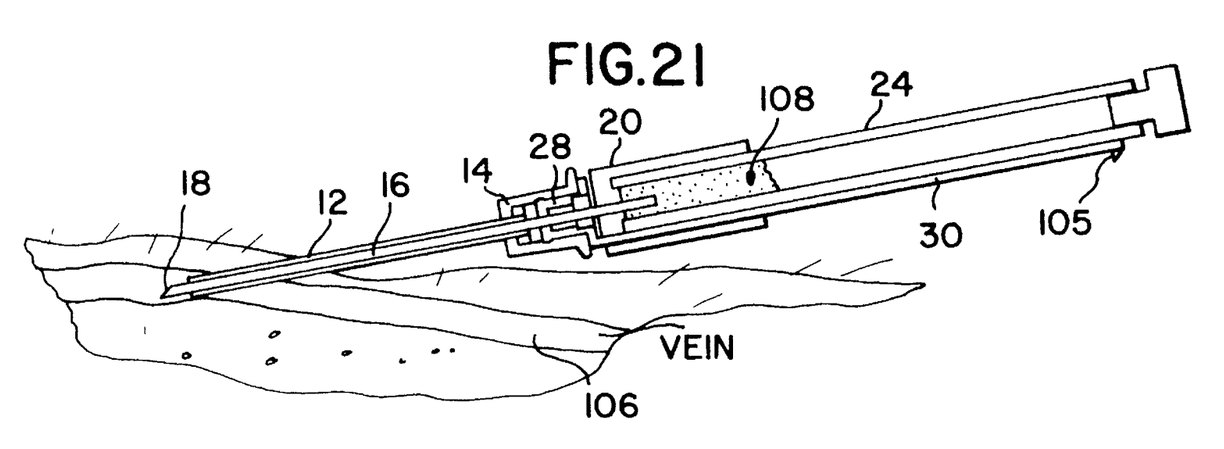
FIGS. 21, 22 and 23 are schematic views showing the operation of the catheter assembly of the present invention including insertion into a vein, withdrawal and protection by the tip guard.
Figure 22:
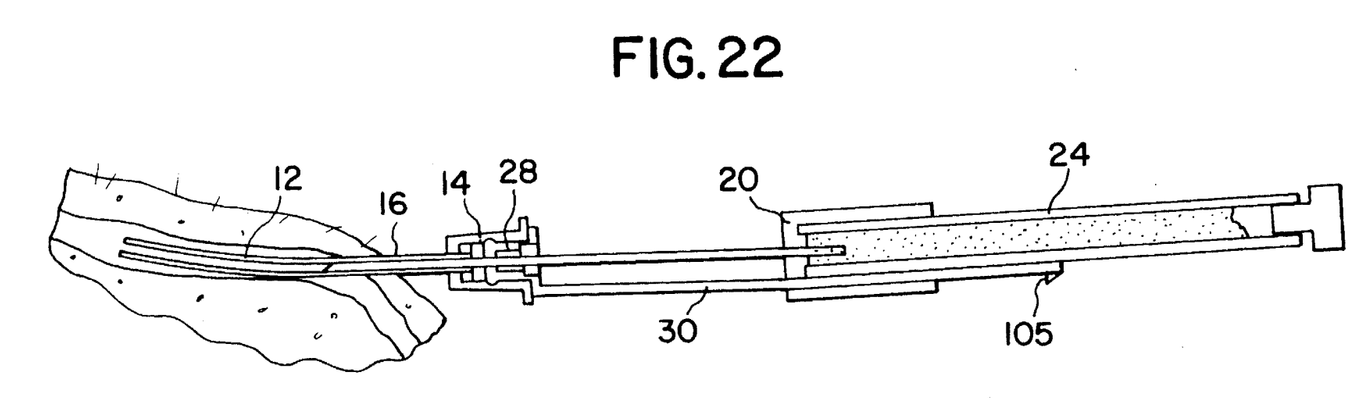
Figure 23:
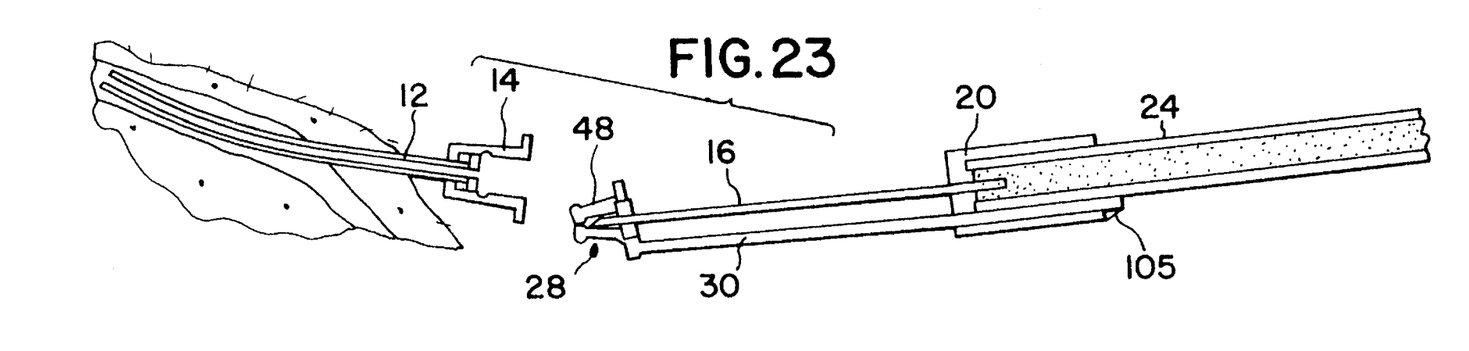

In operation, as shown in FIG. 21, the catheter assembly is initially provided with the cannula extended through the tip guard 28, catheter hub 14 and catheter 12. The catheter 12 and cannula 16 are initially inserted into the vein 106. Once the cannula 16 is inserted into the vein 106, blood will be observed filling the blood chamber 24 as indicated at 108. The cannula 16 can then be threaded into the vein 106, pushing or pulling on the catheter hub 14 or the cannula guard 30 as the catheter hub 14 is still locked to the tip guard 28. Once the catheter 12 is properly placed as shown in FIG. 22, the cannula 16 is then removed from the catheter 12. The withdrawal of the cannula is controlled by the rearward movement of the housing which is limited by the detent 105 on the guard 30. When the cannula 16 passes into the tip guard 28, the fingers 48 collapse releasing the tip guard 28 from the catheter hub 14 automatically protecting the sharp tip 18 as shown in FIG. 23. The catheter 12 and catheter hub 14 are left in the patient and the locked and protected catheter assembly is then disposed of.

While there have been described and illustrated illustrative embodiments of the present invention, it will be apparent to those skilled in the art that variations and modifications are possible without deviating from the spirit and principle of the present invention which shall be limited solely by the scope of the claims appended hereto.

What is claimed is:

1. A catheter assembly comprising:

a catheter attached to a catheter hub;

a cannula having a distal tip, said cannula being insertable into said catheter through said catheter hub;

a tip guard having a base and a plurality of resilient fingers extending from said base, said plurality of fingers being spring biased so that a distal end of each of said fingers is in contact thereby forming a closed chamber within said tip guard, said fingers being adapted to flex radially outwardly to permit the cannula to be inserted into said catheter hub through said tip guard, said fingers returning to the spring biased contact position when the distal tip of the cannula is withdrawn from the catheter into the tip guard thereby securing the distal tip within the closed chamber; and locking means engaging said tip guard to said catheter hub when the cannula is inserted through said catheter hub, said locking means being adapted to release said tip guard from said catheter hub when the distal tip of the cannula is withdrawn from said catheter into said tip guard.

2. The catheter assembly of claim 1 wherein said locking means includes a detent on the distal ends of said fingers and a corresponding recess on the catheter hub.

3. The catheter assembly of claim 1, further including a cannula housing engaging said cannula on a proximal end of the cannula, a blood flash chamber attached to said cannula housing and a cannula guard.

4. The catheter assembly of claim 3 wherein said cannula guard is attached to said tip guard.

5. The catheter assembly of claim 4 wherein said cannula guard extends radially over a portion of said cannula.

6. The catheter assembly of claim 5 wherein said cannula guard extends radially over less than half of the circumference of the cannula.

7. A catheter assembly comprising:

a catheter attached to a catheter hub;

a cannula having a distal tip, said cannula being insertable into said catheter through said catheter hub;

a tip guard having a base and a plurality of resilient fingers extending from said base, said plurality of fingers being spring biased to form a passageway from the base to a distal end of each finger, said passageway having a diameter smaller that the diameter of the cannula, each of said fingers having a channel extending from the base to a location spaced from the distal end, the channels of the fingers forming a chamber having a diameter substantially equal to the diameter of the cannula, said fingers being adapted to flex radially outwardly to permit the cannula to be inserted into said catheter hub through said tip guard, said fingers returning to the spring biased position when the distal tip of the cannula is withdrawn from the catheter into the tip guard thereby securing the distal tip within the chamber to prevent the distal tip of the cannula from being reinserted through the distal ends of the tip guard fingers; and locking means engaging said tip guard to said catheter hub when the cannula is inserted through said catheter hub, said locking means being adapted to release said tip guard from said catheter hub when the distal tip of the cannula is withdrawn from said catheter into said tip guard.

8. The catheter assembly of claim 7 wherein said locking means includes a detent on the distal ends of said fingers and a corresponding recess on the catheter hub.

9. The catheter assembly of claim 7, further including a cannula housing engaging said cannula on a proximal end of the cannula, a blood flash chamber attached to said cannula housing and a cannula guard.

10. The catheter assembly of claim 9 wherein said cannula guard is attached to said tip guard.

11. The catheter assembly of claim 10 wherein said cannula guard extends radially over a portion of said cannula.

12. The catheter assembly of claim 11 wherein said cannula guard extends radially over less than half of the circumference of the cannula.

* * * * *